US012239809B2

(12) United States Patent
Huenerfauth et al.

(10) Patent No.: US 12,239,809 B2
(45) Date of Patent: Mar. 4, 2025

(54) SURGICAL SKIN PREPARATION DEVICE WITH TIMED INDICATOR

(71) Applicant: Becton, Dickinson and Company, Franklin Lakes, NJ (US)

(72) Inventors: Angela Marie Huenerfauth, Morris Plains, NJ (US); Kevin M. Ryan, Whitehouse Station, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/888,774

(22) Filed: Aug. 16, 2022

(65) Prior Publication Data

US 2023/0166091 A1    Jun. 1, 2023

Related U.S. Application Data

(60) Provisional application No. 63/234,097, filed on Aug. 17, 2021.

(51) Int. Cl.
*A61M 35/00* (2006.01)
(52) U.S. Cl.
CPC ....... *A61M 35/006* (2013.01); *A61M 2210/04* (2013.01)
(58) Field of Classification Search
CPC ... A45D 34/04; A61M 35/003; A61M 35/006; A61M 35/00; A61F 2013/15487; A61F 13/38
See application file for complete search history.

(56) References Cited

U.S. PATENT DOCUMENTS

| | | | | | |
|---|---|---|---|---|---|
| 4,183,684 | A | * | 1/1980 | Avery, Jr. | A45D 34/04 401/133 |
| 4,415,288 | A | * | 11/1983 | Gordon | A47K 7/028 401/133 |
| 4,498,796 | A | * | 2/1985 | Gordon | A47K 7/03 604/3 |
| 4,507,111 | A | * | 3/1985 | Gordon | A47L 13/24 604/3 |
| 4,528,268 | A | * | 7/1985 | Andersen | C12Q 1/22 435/31 |

(Continued)

FOREIGN PATENT DOCUMENTS

| | | | | |
|---|---|---|---|---|
| EP | 0600508 A1 | * | 12/1993 | A61M 35/00 |
| WO | WO-9413352 A1 | * | 6/1994 | A45D 34/04 |

(Continued)

*Primary Examiner* — Susan S Su
*Assistant Examiner* — Ted Yang
(74) *Attorney, Agent, or Firm* — The Webb Law Firm

(57) ABSTRACT

A surgical skin preparation device for applying an antiseptic composition to skin of a patient includes an applicator configured to absorb the antiseptic composition, the applicator having a top surface and a bottom surface, the bottom surface configured to apply the antiseptic composition to the skin of the patient, and an indicator. The indicator includes a first layer of a first material configured to wick the antiseptic composition, the first material being opaque in a first state and transparent or translucent in a second state, and a second layer of a non-wettable material, the second layer having at least one indicia that is visible to a user when the first layer is in the second state.

18 Claims, 6 Drawing Sheets

(56) References Cited

U.S. PATENT DOCUMENTS

| | | | | |
|---|---|---|---|---|
| 4,925,327 A * | 5/1990 | Wirt | ............... | B65D 47/42 |
| | | | | 604/3 |
| 4,957,385 A * | 9/1990 | Weinstein | ........... | A61M 35/006 |
| | | | | 604/3 |
| 5,308,180 A * | 5/1994 | Pournoor | ............... | B01D 69/02 |
| | | | | 604/3 |
| 5,435,660 A * | 7/1995 | Wirt | ................ | A61M 35/006 |
| | | | | 604/3 |
| 5,445,462 A * | 8/1995 | Johnson | ............ | A61M 35/006 |
| | | | | 401/133 |
| 5,489,280 A * | 2/1996 | Russell | ............... | A61M 35/003 |
| | | | | 604/289 |
| 6,501,002 B1 * | 12/2002 | Roe | ................... | G01N 33/528 |
| | | | | 422/402 |
| 6,916,133 B2 * | 7/2005 | Hoang | ................ | A61M 35/006 |
| | | | | 401/133 |
| 9,750,922 B2 * | 9/2017 | Hoang | .................. | B65B 51/10 |
| 10,576,256 B2 | 3/2020 | Souza et al. | | |
| 2004/0150527 A1 * | 8/2004 | Harper | ................. | A61B 90/80 |
| | | | | 340/573.1 |
| 2004/0179888 A1 * | 9/2004 | Tufts | ................... | B05C 17/002 |
| | | | | 401/133 |
| 2006/0039742 A1 * | 2/2006 | Cable, Jr. | ............ | A61M 35/003 |
| | | | | 401/133 |
| 2006/0072959 A1 * | 4/2006 | Tufts | .................... | B05C 17/002 |
| | | | | 401/133 |
| 2013/0202482 A1 * | 8/2013 | Froimson | ............ | A61M 35/006 |
| | | | | 401/194 |
| 2014/0371695 A1 * | 12/2014 | Chiang | ............... | A61M 35/006 |
| | | | | 604/310 |
| 2016/0228686 A1 * | 8/2016 | Dombrowski | ...... | A61M 35/006 |
| 2018/0161560 A1 * | 6/2018 | Souza | .................... | A61B 90/80 |
| 2018/0333566 A1 * | 11/2018 | Follman | ................. | A01N 47/44 |
| 2019/0159572 A1 * | 5/2019 | Tarajano | ............. | A61M 35/003 |
| 2019/0170543 A1 * | 6/2019 | Rothenberg | ......... | G01N 31/226 |
| 2019/0209816 A1 * | 7/2019 | Follman | .............. | A61M 35/006 |
| 2019/0269894 A1 * | 9/2019 | Yarger | ................. | A61L 2/0088 |
| 2019/0298584 A1 * | 10/2019 | Mayfield | ................ | B32B 27/36 |
| 2020/0164616 A1 * | 5/2020 | Carlyle | .................. | B32B 7/12 |
| 2021/0299422 A1 * | 9/2021 | McLelan | .............. | A61M 35/006 |
| 2023/0301746 A1 * | 9/2023 | McGinley | ............ | A61L 2/0088 |
| | | | | 604/290 |

FOREIGN PATENT DOCUMENTS

| | | | | |
|---|---|---|---|---|
| WO | WO-2018031240 A1 * | 2/2018 | ......... | A61M 35/006 |
| WO | 2020028289 A1 | 2/2020 | | |

* cited by examiner

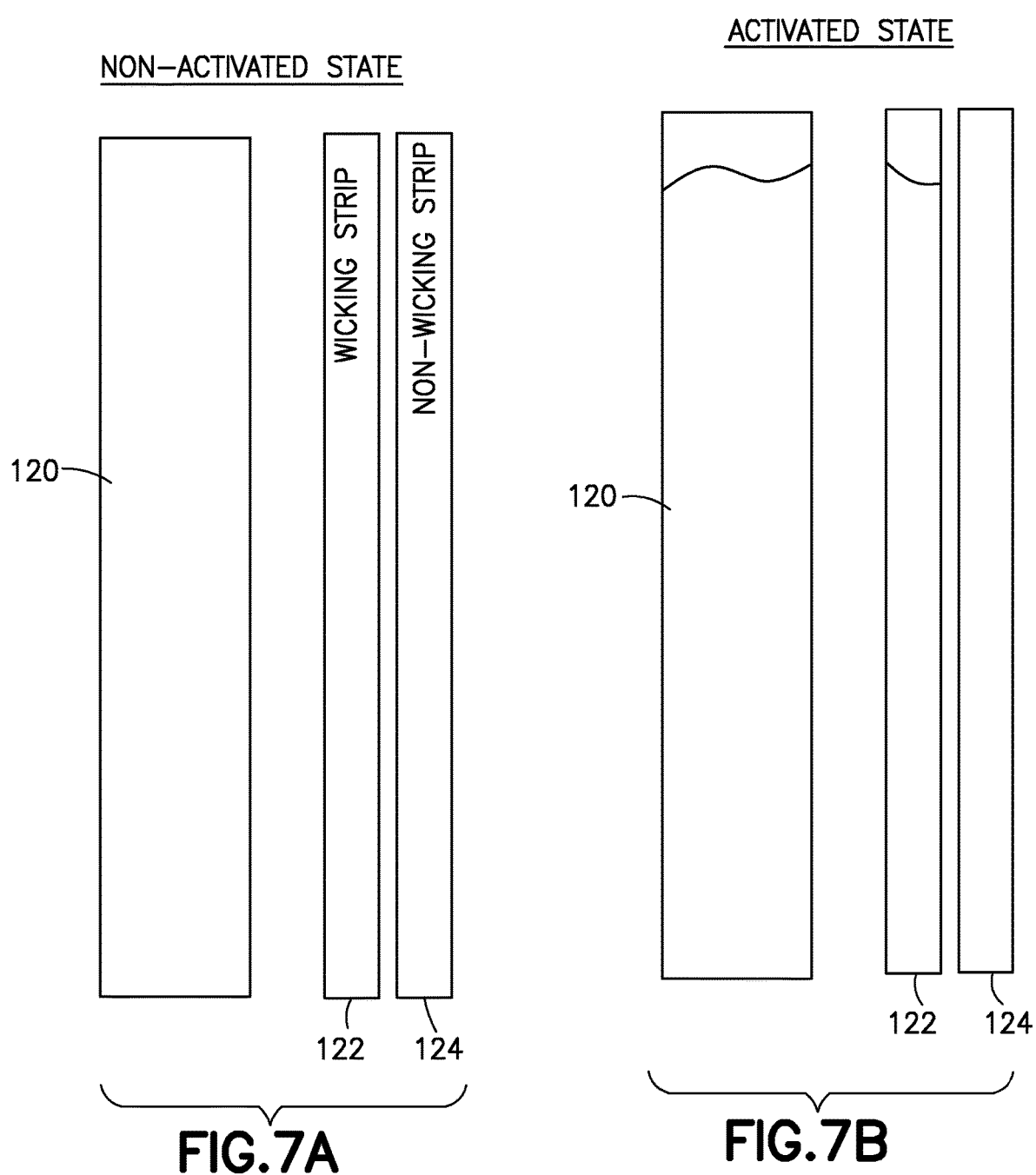

SURGICAL SKIN PREPARATION DEVICE WITH TIMED INDICATOR

CROSS-REFERENCE TO RELATED APPLICATION

The present application claims priority to U.S. Provisional Application Ser. No. 63/234,097, filed Aug. 17, 2021, entitled "Surgical Skin Preparation Device with Timed Indicator", the entire disclosure of which is hereby incorporated by reference in its entirety.

BACKGROUND OF THE INVENTION

Field of the Invention

The present invention relates to an indicating device for use with surgery preparation. More particularly, the invention relates to the use of an indicator for use with a surgical skin preparation device that allows a user to know that a predetermined, adequate duration of scrubbing has been applied to the surgical site.

Description of Related Art

Proper cleansing and disinfecting a surgical site is crucial to reduce the likelihood of adverse events, including infection, during and following the intervention. However, for many reasons ranging from pressure to rapidly prepare a patient for surgery to distractions inherent in the environment, many clinicians and other surgical staff do not engage in proper cleansing and disinfecting techniques, for example such as the suggested guidelines of 30 seconds of cleansing, followed by 30 seconds of drying for dry skin areas.

Accordingly, there is a need in the art for improved devices and methods for properly preparing a site for a surgical intervention.

SUMMARY OF THE INVENTION

In accordance with an embodiment of the present invention, a surgical skin preparation device for applying an antiseptic composition to skin of a patient includes an applicator configured to absorb the antiseptic composition. The applicator includes a top surface and a bottom surface, the bottom surface configured to apply the antiseptic composition to the skin of the patient. The surgical preparation device also includes an indicator including a first layer having a first material configured to wick the antiseptic composition, wherein the first material is opaque in a first state and is transparent or translucent in a second state, and a second layer including a non-wettable material, the second layer including at least one indicia that is visible to a user when the first layer is in the second state.

The indicator may be arranged on the top surface of the applicator and the second layer of the indicator may be arranged between the top surface of the applicator and the first layer of the indicator. Optionally, the device may include a handle having a proximal end and a distal end, wherein the applicator is arranged at the distal end of the handle. The indicator may be arranged at the distal end of the handle and the second layer of the indicator is arranged between the top surface of the applicator and the first layer of the indicator. The handle may be configured to store the antiseptic composition. Optionally, the handle defines a pathway that fluidly connects the antiseptic composition and the applicator. The antiseptic composition may be stored in a frangible or pierceable container.

In other configurations, the handle may include one or more actuable elements configured to break or pierce the container. In certain configurations, the first layer is in the first state when the antiseptic composition has not been wicked along the first layer, and the first layer is in the second state when the antiseptic composition has been wicked along more than about 50%, optionally more than about 75%, optionally more than about 90% of the first layer. Optionally, the first material is configured such that the antiseptic composition is wicked along most of the length, or the full length, of the first layer about 30 seconds following initial exposure to the antiseptic composition.

The first layer may be configured to progressively change from the first state to the second state as the antiseptic composition is wicked from a first end of the first layer to a second end of the first layer. The first material may be configured such that the antiseptic composition is wicked across more than about 50%, optionally more than about 75%, optionally more than about 90% of the first layer about 30 seconds following initial exposure to the antiseptic composition. In certain configurations, the applicator is circular in shape. In other configurations, the applicator is quadrilateral in shape. Optionally, the indicia comprises one or more of a color and a symbol.

In accordance with another embodiment of the present invention, a method of disinfecting skin includes applying an antiseptic composition to the skin of a patient with a device until the indicia is at least partially visible to a user. The device includes an applicator configured to absorb the antiseptic composition. The applicator includes a top surface and a bottom surface, the bottom surface configured to apply the antiseptic composition to the skin of the patient. The surgical preparation device also includes an indicator including a first layer having a first material configured to wick the antiseptic composition, wherein the first material is opaque in a first state and is transparent or translucent in a second state, and a second layer including a non-wettable material, the second layer including at least one indicia that is visible to a user when the first layer is in the second state.

The method may also include that the antiseptic composition is applied to the skin of the patient for at least 30 seconds before the indicia is at least partially visible to the user.

In accordance with another embodiment of the present invention, a method of disinfecting skin includes providing a device having a handle having a proximal end, a distal end, a sidewall therebetween, and one or more actuable elements arranged along the sidewall, the sidewall defining an at least partially hollow interior. The device also includes a frangible or pierceable container holding an antiseptic composition received within the at least partially hollow interior, the container configured to be broken or pierced by the one or more actuable elements. The device also includes an applicator arranged at the distal end of the handle and in fluid communication with the at least partially hollow interior, the applicator configured to, following breaking or piercing of the container, absorb the antiseptic composition, the applicator comprising a top surface and a bottom surface, the bottom surface configured to apply the antiseptic composition to the skin of the patient. The device further includes an indicator having a first layer including a first material configured to wick the antiseptic composition, wherein the first material is opaque when dry and is transparent or translucent when wet, and a second layer including a non-wettable material, the second layer including at least one indicia that is visible to a user when the first layer is wet. The method further includes the steps of actuating the one or more actuable elements to break or pierce the container, and applying the antiseptic composition to the skin of the patient until the indicia is at least partially visible.

In accordance with yet another embodiment of the present invention, a device includes a handle including a proximal end, a distal end, a sidewall therebetween, and one or more actuable elements arranged along the sidewall, with the sidewall defining an at least partially hollow interior. The device further includes a frangible or pierceable container holding an antiseptic composition received within the at least partially hollow interior, the container configured to be broken or pierced by the one or more actuable elements. The device further includes a circular applicator arranged at the distal end of the handle and in fluid communication with the at least partially hollow interior, the applicator configured to, following breaking or piercing of the container, absorb the antiseptic composition, the applicator comprising a top surface and a bottom surface, the bottom surface configured to apply the antiseptic composition to the skin of the patient. The device also include an indicator arranged at least partially on the top surface of the applicator. The indicator includes a first layer in fluid communication with the applicator and including a first material configured to wick the antiseptic composition, wherein the first material is opaque when dry and is transparent or translucent when wet. The indicator also includes a second layer arranged between the first layer and the applicator and including a non-wettable material, the second layer including at least one indicia that is visible to a user when the first layer is wet.

In accordance with yet another embodiment, a device includes a handle having a proximal end, a distal end, a sidewall therebetween, and one or more actuable elements arranged along the sidewall, with the sidewall defining an at least partially hollow interior. The device also includes a frangible or pierceable container holding an antiseptic composition received within the at least partially hollow interior, the container configured to be broken or pierced by the one or more actuable elements. The device also includes a quadrilateral applicator arranged at the distal end of the handle and in fluid communication with the at least partially hollow interior, the applicator configured to, following breaking or piercing of the container, absorb the antiseptic composition, the applicator including a top surface and a bottom surface, the bottom surface configured to apply the antiseptic composition to the skin of the patient. The device further includes an indicator arranged at least partially on the top surface of the applicator and including a first layer in fluid communication with the applicator and including a first material configured to wick the antiseptic composition, wherein the first material is opaque when dry and is transparent or translucent when wet. The indicator further includes a second layer arranged between the first layer and the applicator and including a non-wettable material, the second layer including at least one indicia that is visible to a user when the first layer is wet.

BRIEF DESCRIPTION OF THE DRAWINGS

FIG. 7A is a schematic view of an indicator according to non-limiting embodiments or aspects as described herein; and FIG. 7B is a schematic view of an indicator according to non-limiting embodiments or aspects as described herein.

DESCRIPTION OF THE INVENTION

Figure 1B:
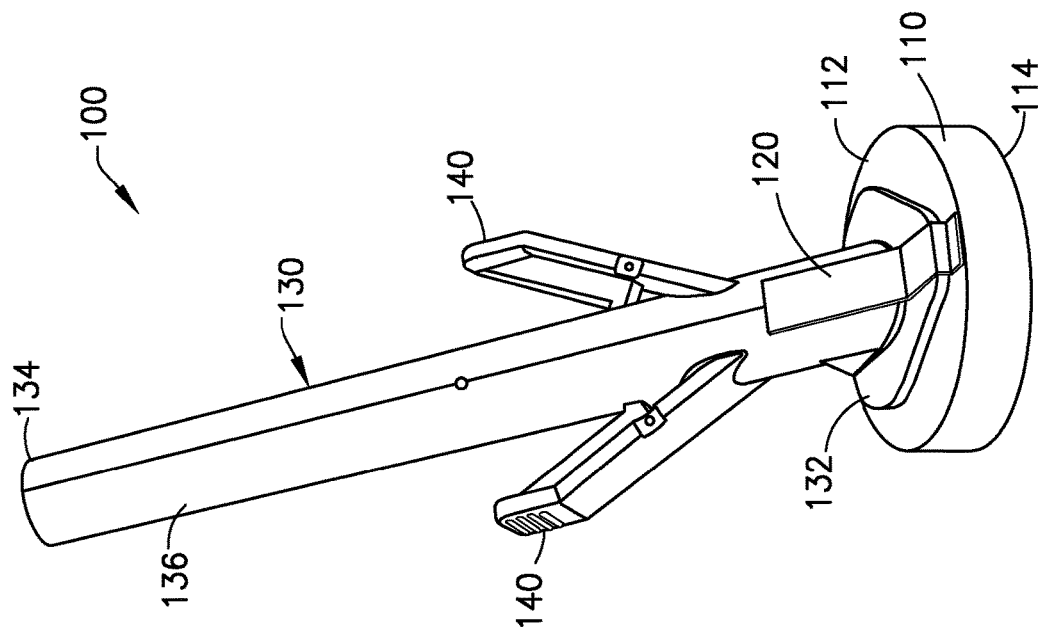
FIG. 1B is a perspective view of a device including an indicator according to non-limiting embodiments or aspects as described herein.
Figure 1A:
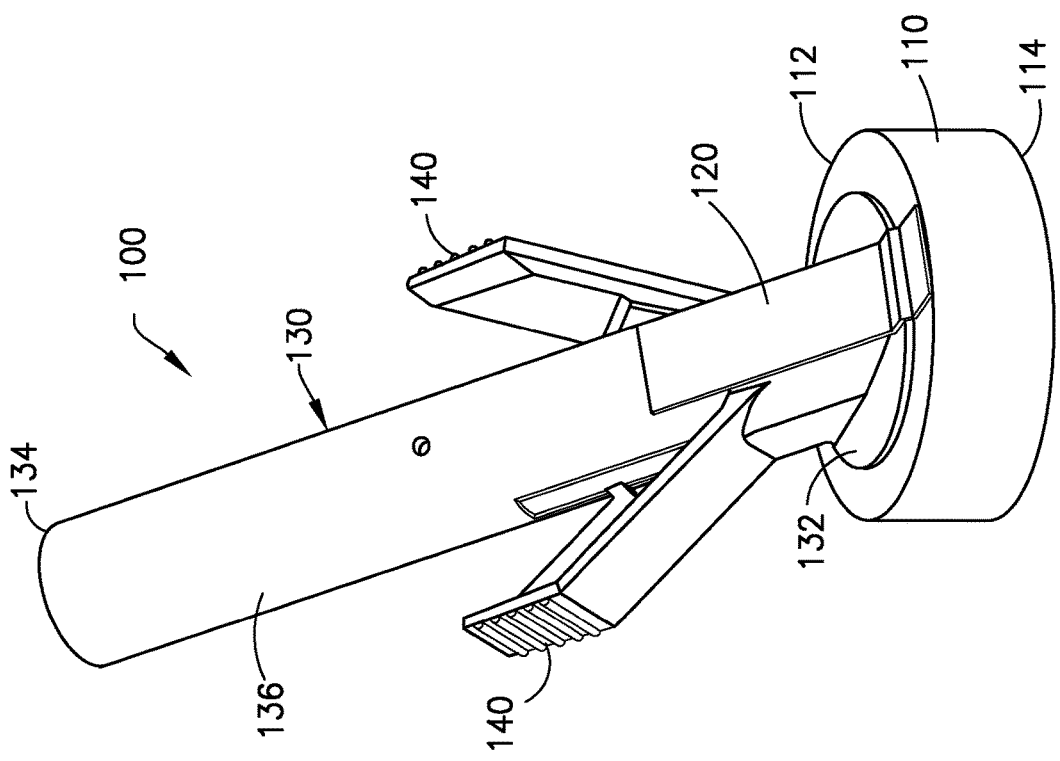
FIG. 1A is a perspective view of a device including an indicator according to non-limiting embodiments or aspects as described herein.
Figure 2A:
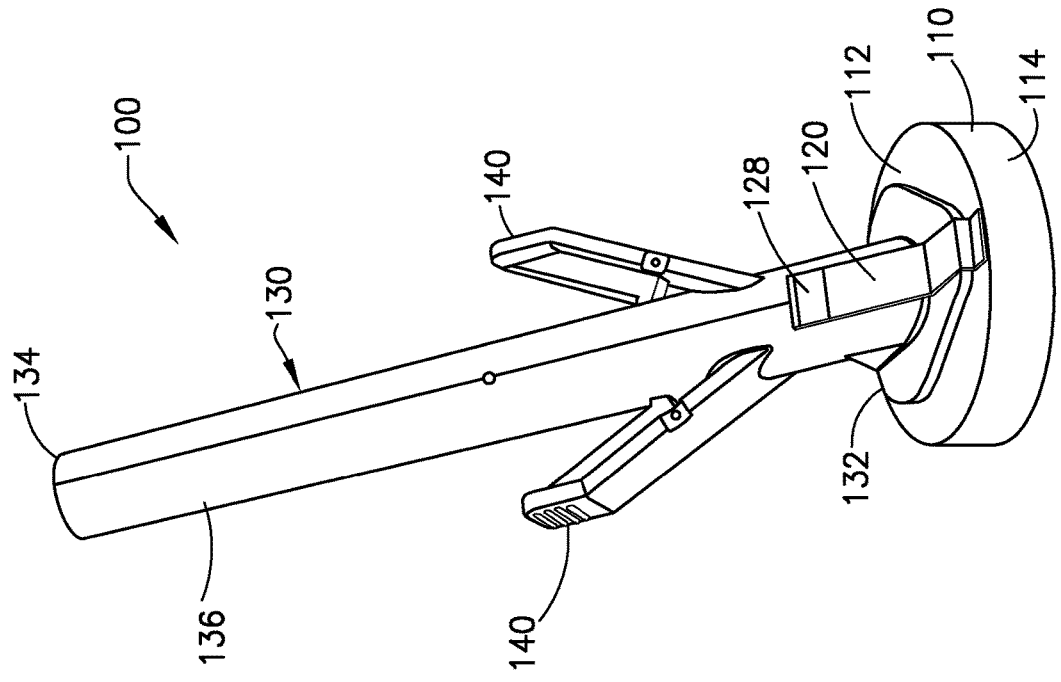
FIG. 2A is a perspective view of a device including an indicator according to non-limiting embodiments or aspects as described herein.
Figure 2B:
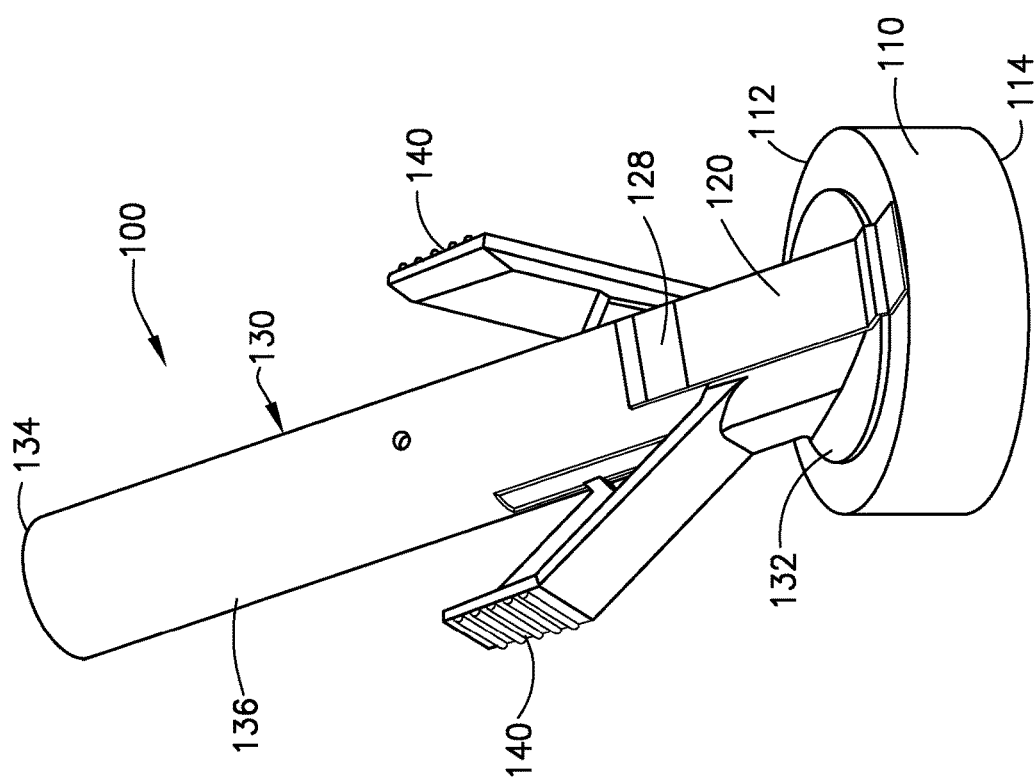
FIG. 2B is a perspective view of a device including an indicator according to non-limiting embodiments or aspects as described herein.
Figure 4:
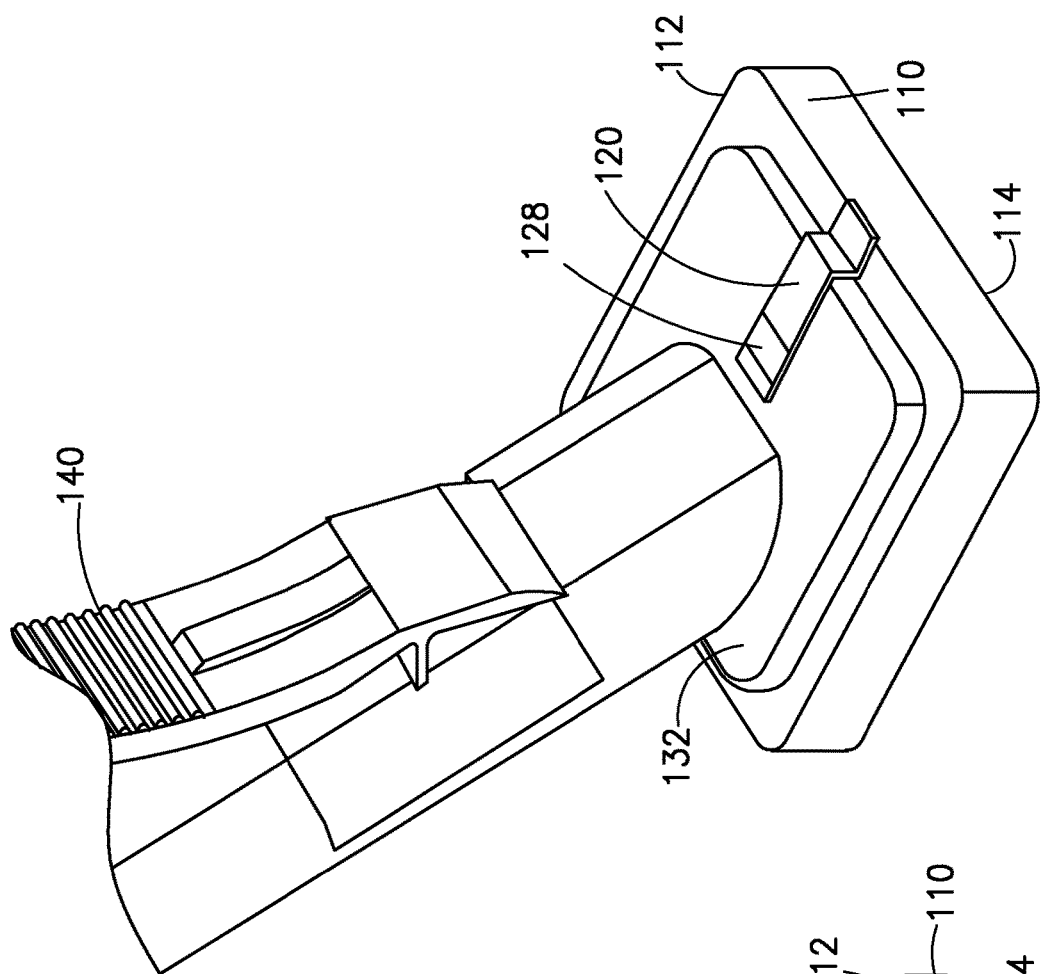
FIG. 4 is an enlarged perspective view of a device including an indicator according to non-limiting embodiments or aspects as described herein.
Figure 3:
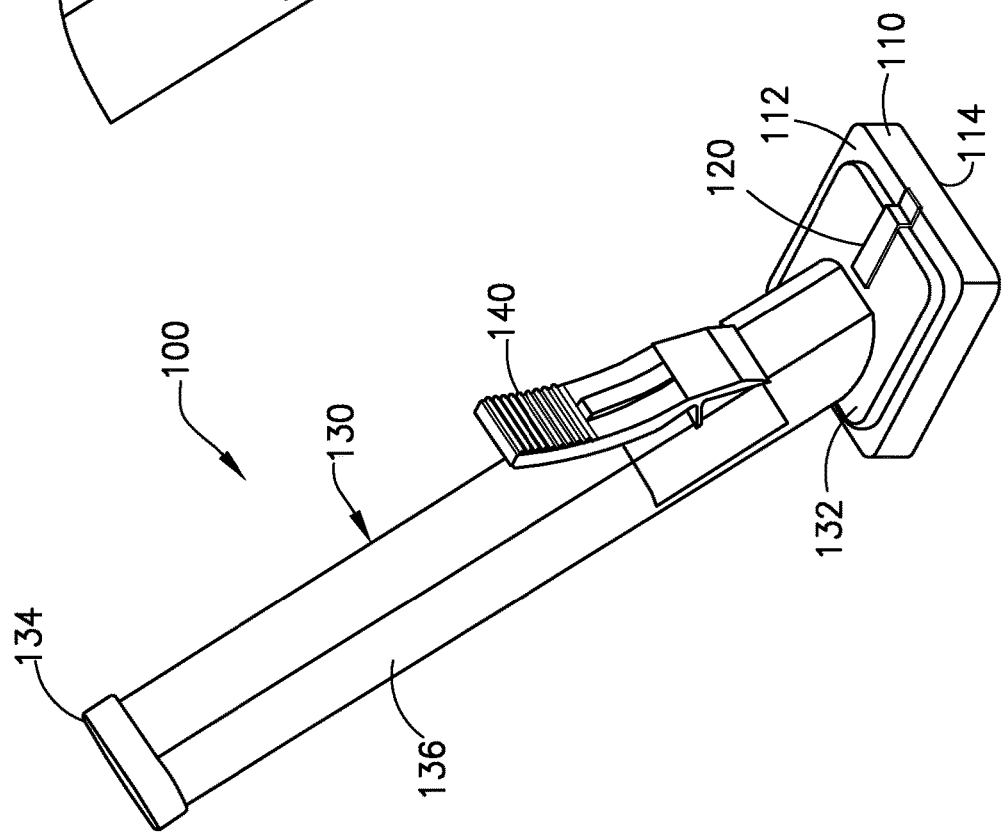
FIG. 3 is a perspective view of a device including an indicator according to non-limiting embodiments or aspects as described herein.

The following description is provided to enable those skilled in the art to make and use the described aspects contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

The figures accompanying this application are representative in nature, and should not be construed as implying any particular scale or directionality, unless otherwise indicated. For purposes of the description hereinafter, the terms "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations and step sequences, except where expressly specified to the contrary. Hence, specific dimensions and other physical characteristics related to the embodiments disclosed herein are not to be considered as limiting.

Provided herein is a device for applying an antiseptic composition to skin of a patient, for example for preparing an area of the patient's skin for a surgical intervention. As used herein, the term "patient" is any animal, including humans, and a "human patient" is any human. As used herein, the term "antiseptic composition" is any composition that prevents or inhibits the growth of one or more microorganisms.

In non-limiting embodiments or aspects, the antiseptic composition includes one or more alcohols, such as ethyl alcohol, propyl alcohol, isopropyl alcohol, n-propanol, and/or mixtures thereof. In non-limiting embodiments or aspects, the antiseptic composition includes one or more non-alcohol based compounds, such as iodine, para-chloro-meta-xylenol, bis-biguanides such as chlorhexidine gluconate (CHG)), chlorhexidine diacetate or quaterium class compounds such as benzethonium chloride, benzalkonium chloride, chloroxylenol, triclosan, hexachlorophenes, octenidine, diazolidinyl urea, methyl chloro isothiazoline, methyl isothiazoline, triclosan, and/or mixtures thereof. In non-limiting embodiments or aspects, the antiseptic composition includes a mixture of any of the aforementioned, including mixtures of alcohol and non-alcohol based compounds. In non-limiting embodiments or aspects, the antiseptic composition includes CHG and an alcohol, for example isopropyl alcohol. In non-limiting embodiments or aspects, the antiseptic composition includes about 2% (w/v) CHG and about 70% (v/v) isopropyl alcohol.

In non-limiting embodiments or aspects, the antiseptic composition is effective against one or more microorganisms, such as bacteria, viruses, and/or fungi. In non-limiting embodiments or aspects, the microorganism is one or more of coagulase-negative staphylococci, *Staphylococcus aureus* (including methicillin-resistant *S. aureus*), *Enterococcus* spp. (including vancomycin-resistant *Enterococci*, such as *E. faecium*), *Candida* spp., *Escherichia coli* (including extended-spectrum cephalosporin resistant *E. coli* and carbanpenem-resistant *E. coli*), *Closrtridium difficile*, *Pseudomonas aeruginosa* (including carbapenem-resistant *P. aeruginosa*), *Klebsiella pneumoniae* (including extended-spectrum cephalosporin-resistant *K. pneumoniae* and carbapenem-resistant *K. pneumoniae*), *Enterobacter* spp., *Acinetobacter* spp. (including *Acinetobacter baumannii*), and *Klebsiella oxytoca*.

As used herein, the term "surgical intervention" means any percutaneous treatment (e.g., catheterization, angioplasty, needle biopsy, and the like), open surgery, laparoscopic surgery, and/or minimally-invasive surgery that involves puncturing the skin or creating one or more incisions of varying size in the skin of the patient.

Turning to FIGS. 1-6, shown is an exemplary, non-limiting embodiment or aspect of a device 100 for applying an antiseptic composition to skin of a patient. Device 100 includes an applicator 110, such as a sponge or other porous, absorbent material that is configured to hold the antiseptic composition, and to allow a user to apply the antiseptic composition to the patient's skin at the site of the surgical intervention and, optionally, one or more areas adjacent to the site of the surgical intervention. Applicator 110 can be a natural sponge, a synthetic sponge including, for example and without limitation, a polyurethane, a polyester, and/or a vegetal cellulose, or other suitable material, so long as the material is capable of absorbing and/or dispensing the antiseptic composition. Applicator 110 can have a top surface 112 and a bottom surface 114. Either surface can be used to apply the antiseptic composition to the patient's skin; however, for simplicity, the device 100 will be described herein with reference to the bottom surface 114 as the surface that is configured to come into contact with the patient's skin.

Figure 5:
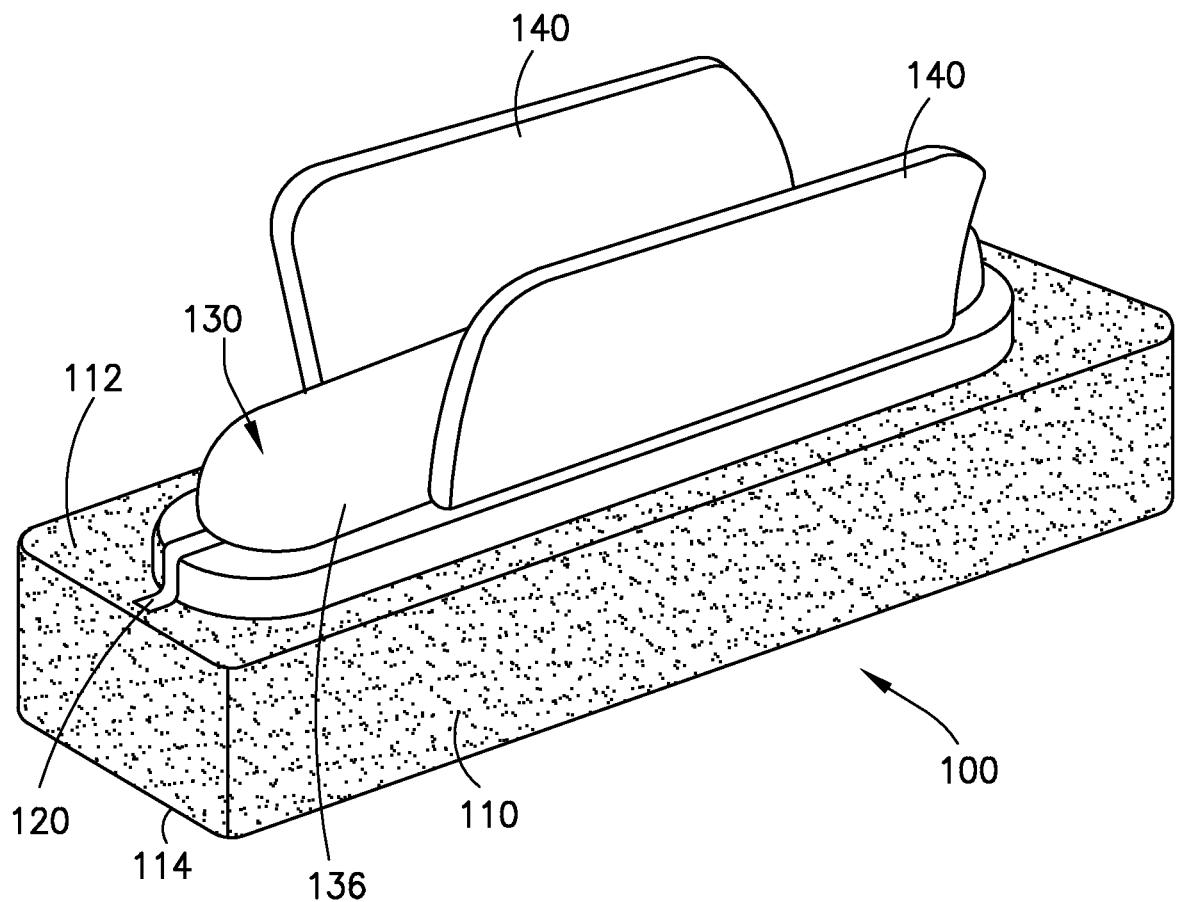
FIG. 5 is a perspective view of a device including an indicator according to non-limiting embodiments or aspects as described herein.

In non-limiting embodiments or aspects, device 100 includes a handle 130 to allow a user to apply the antiseptic composition to the skin of a patient, while maintaining aseptic technique (e.g., by not directly contacting the applicator). In non-limiting embodiments or aspects, handle 130 can be configured with a distal 132 and proximal 134 end, and a sidewall 136 therebetween, with applicator 110 arranged at the distal end 132, for example as shown in FIGS. 1-4 and 6. In non-limiting embodiments or aspects, handle 130 can be arranged as shown in FIG. 5, where the handle sidewall 136 is in contact with applicator 110. Handle 130 can be formed of any useful material, such as a metal, metal alloy, and/or plastic.

Figure 6:
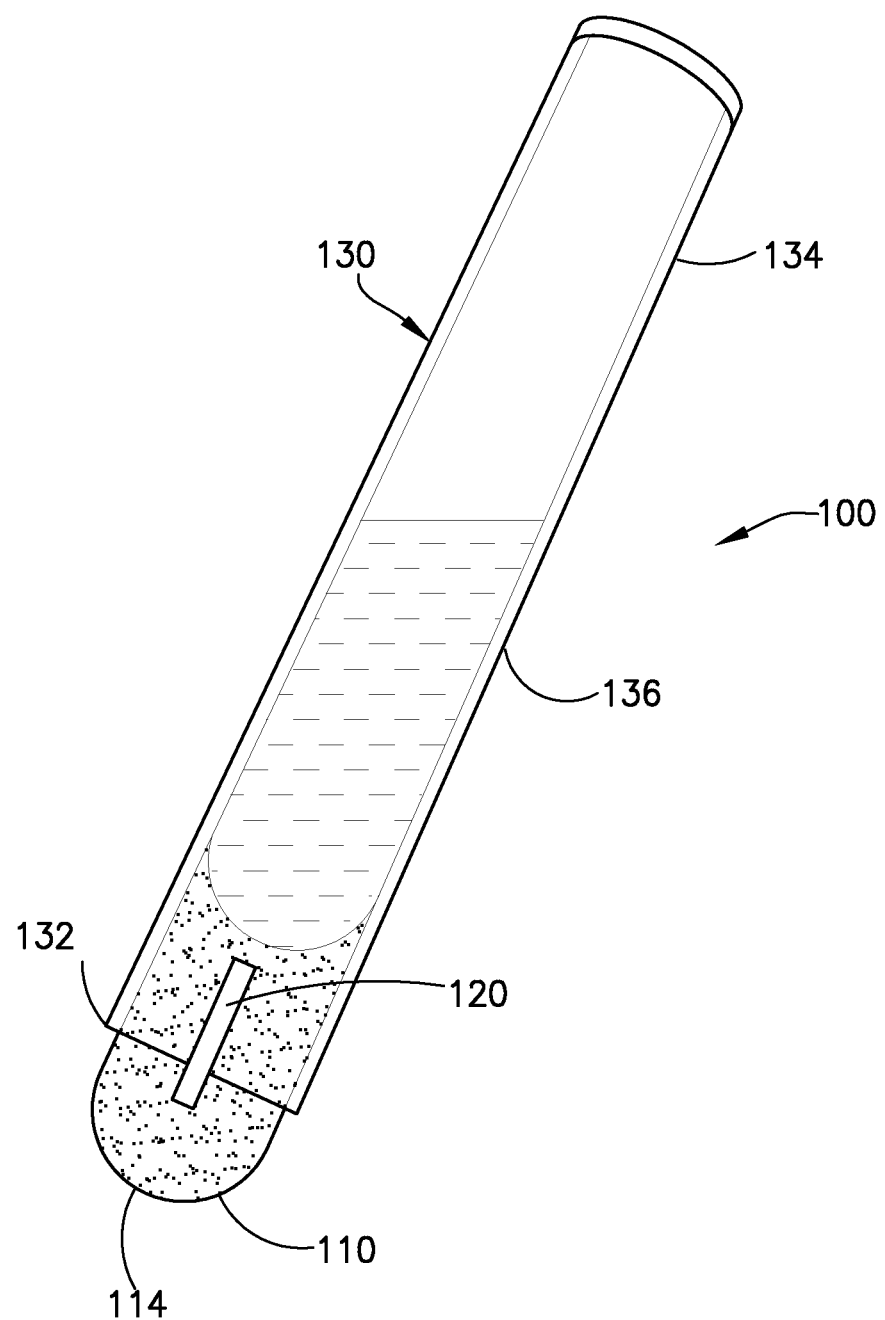
FIG. 6 is a perspective view of a device including an indicator according to non-limiting embodiments or aspects as described herein.

In non-limiting embodiments or aspects, handle 130 is at least partially hollow, and is configured to hold the antiseptic composition therein, and to allow fluid communication between the antiseptic composition held therein and applicator 110. In this way, device 100 can be provided as a sterilized package, with device 100 and the antiseptic composition pre-packaged as a single unit. In non-limiting embodiments or aspects, the antiseptic composition is stored within a container held within handle 130, such that applicator 110 is not in contact with the antiseptic composition during storage/before use. In non-limiting embodiments or aspects, the container is a frangible or pierceable container, formed of glass, plastic, or other suitable material. Such an arrangement allows a user to control initiation of contact between the antiseptic composition and applicator 110. In non-limiting embodiments or aspects, for example as shown in FIG. 6, sidewall 136 of handle 130 can be flexible and/or resilient, such that a user can apply a radially-inward pressure to the sidewall 136 to cause the container to break or be pierced.

In non-limiting embodiments or aspects, handle 130 includes one or more actuable elements 140, that, when actuated, can cause the container within handle 130 to be broken or pierced, thereby allowing the antiseptic composition to come into contact with applicator 110. Actuable element(s) 140 can take any useful form, for example, and without limitation, the form shown in FIGS. 1-5, so long as they are capable of being actuated by a user to cause release of the antiseptic composition. Actuable element(s) 140 can include ergonomic features and/or features to improve a user's grip and/or reduce slippage, such as texturing.

With continuing reference to the figures, device 100 includes indicator 120 configured to alert a user that the antiseptic composition has been applied to the skin for an adequate amount of time. As shown in FIGS. 7A and 7B, indicator 120 includes first layer 122 and second layer 124. First layer 122 is arranged superficial to second layer 124 when viewed from the perspective of a user. For example, in the non-limiting embodiment or aspect illustrated in FIGS. 1-4, second layer (not visible) is arranged between first layer of indicator 120 and applicator 110. In non-limiting embodiment or aspects, indicator 120 is arranged such that first layer 122 is larger (e.g., has a larger perimeter) than second layer 124, such that first layer 122 can be in fluid communication with applicator 110. By assuming this configuration, first layer 122 can come into contact with the antiseptic composition in applicator 110. In non-limiting embodiments or aspects, indicator 120 is arranged at a distal end of handle 130 (or at an edge of handle 130, for example in the embodiment illustrated in FIG. 5). Those of skill in the art will appreciate that indicator 120 can be arranged in any useful manner, so long as first layer 122 can be in fluid communication with the antiseptic composition.

First layer 122 can be formed of material that can, for example through capillary action (e.g., wicking), transport the antiseptic composition from a first end of the layer (e.g., which is in fluid communication with the antiseptic composition, for example by virtue of being in contact with applicator 100) to an opposite, second end, for example as shown in FIGS. 7A and 7B. In non-limiting embodiments or aspects, the first layer is formed of a wettable material. As used herein, the term "wettable" means that the material has a surface with a water contact angle of 75° or less, optionally 60° or less, and is capable of transporting a liquid, such as the antiseptic composition, by capillary action.

First layer 122 can be formed of a material that is opaque, or substantially opaque, when in a first (e.g., dry) state, and translucent or transparent (or substantially translucent or transparent) when in a second (e.g., wet) state. Because in non-limiting embodiments the first layer is formed of a material capable of wicking the antiseptic composition, as the material becomes wet and the antiseptic composition is wicked towards a far end of the indicator, progressively more and more of the first layer becomes wet (and thus transparent or translucent), allowing progressive exposure of the second layer 124 to a user. In non-limiting embodiments or aspects, first layer 122 can be formed of a polymeric material such as polyester, polypropylene, nylon, and/or rayon, and/or natural materials such as paper-based materials, and/or wool, such as Merino wool.

Second layer 124 can be formed of any non-wettable material. As used herein, the term "non-wettable" means that the material has a surface with a water contact angle of 90° or greater. Second layer 124 includes indicia 128 and, because of the variable opaque and translucent and/or transparent nature of first layer 122, indicia 128 is only visible to a user when first layer 122 is partially or fully transparent or translucent (e.g., when the antiseptic composition has been wicked along a portion, or the full length, of the layer). In non-limiting embodiments or aspects, indicia 128 is a coloring that is present on at least a portion of second layer 124, for example by being printed on the layer. In non-limiting embodiments or aspects, the second layer 124 comprises a color along at least a portion, optionally along substantially all of the layer, optionally along the entire layer, such that a greater and greater amount of color is visible as the antiseptic composition is wicked further along the first layer. In non-limiting embodiments or aspects, indicia 128 is a symbol that is present on at least a portion of second layer 124. In non-limiting embodiments or aspects, indicia 128 is provided at an end of the first layer 124 underlying a portion of the first layer 122 that is the last to be brought into contact with the antiseptic composition (due to wicking).

Referring to FIG. 7B, such an end is provided at the top of the image. In this way, indicia 128 is only visible when the antiseptic composition has been wicked along substantially the full length, optionally the full length, of the first layer, thus representing that the antiseptic composition has been applied to the patient's skin for an adequate length of time to provide sufficient disinfection. In non-limiting embodiments or aspects, first layer 122 can be formed of a non-wettable polymeric or paper-based material, including those that are coated to provide a non-wettable characteristic.

Those of skill in the art will appreciate that suitable materials can be selected to provide a predetermined elapsed time when partial and/or full transparency and/or translucency has occurred, corresponding to suitable times for which an antiseptic composition is applied to a site of a surgical intervention. In non-limiting embodiments or aspects, the material is configured such that partial and/or full transparency and/or translucency is achieved about 30 seconds after initial exposure of the indicator 120 to the antiseptic composition.

In non-limiting embodiments or aspects, indicator 120 as described herein can be utilized with an application device, such as those commercially available from Becton, Dickinson and Company under the trademark CHLORAPREP, and/or those described in, for example and without limitation, U.S. Pat. Nos. 6,916,133 and 9,750,922, the contents of which are incorporated herein by reference in their entirety.

Also provided herein are methods of using a device as described above for disinfecting skin. Such methods include a step of applying an antiseptic composition to the skin of a patient with a device as described herein until the indicia 128 is at least partially visible to a user. In non-limiting embodiments or aspects the antiseptic composition is applied to the skin for about 30 seconds before indicia 128 is visible to the user. In non-limiting embodiments or aspects, the method further includes, before applying the antiseptic composition, a step of actuating the one or more actuable elements 140, or squeezing sidewall 136, to release antiseptic composition from a container received within handle 130.

While the present invention has been described in terms of the above detailed description, those of ordinary skill in the art will understand that alterations may be made within the spirit of the invention. Accordingly, the above should not be considered limiting, and the scope of the invention is defined by the appended claims.

The invention claimed is:

1. A surgical skin preparation device for applying an antiseptic composition to skin of a patient, comprising:
   an applicator arranged at a distal end of the device configured to absorb the antiseptic composition, the applicator comprising a top surface and a bottom surface, the bottom surface defining the distal most end of the device and configured to apply the antiseptic composition to the skin of the patient; and
   an indicator comprising:
      a first layer comprising a first material configured to wick the antiseptic composition, wherein the first material is opaque in a first state and is transparent or translucent in a second state; and
      a second layer comprising a non-wettable material, the second layer comprising at least one indicia that is visible to a user when the first layer is in the second state,
      wherein the first layer is configured to progressively change from the first state to the second state as the antiseptic composition is wicked from a first end of the first layer to a second end of the first layer, with the first layer becoming more wet as the composition is wicked from the first end to the second end, allowing progressive exposure of the second layer,
      wherein the first layer is in the first state when the antiseptic composition has not been wicked along the first layer, and the first layer is in the second state when the antiseptic composition has been wicked along more than about 50% of the first layer, and
      wherein the first material is a wettable material having a surface with a water contact angle of 75 degrees or less and the first material is configured such that the antiseptic composition is wicked across more than about 50% of the first layer about 30 seconds following initial exposure of the first material to the antiseptic composition,
      wherein the indicator is arranged on the top surface of the applicator and the second layer of the indicator is arranged between the top surface of the applicator and the first layer of the indicator.

2. The device according to claim 1, further comprising a handle having a proximal end and a distal end, and wherein the applicator is arranged at the distal end of the handle.

3. The device according to claim 2, wherein the indicator is arranged at the distal end of the handle and the second layer of the indicator is arranged between the top surface of the applicator and the first layer of the indicator.

4. The device according to claim 2, wherein the handle is configured to store the antiseptic composition.

5. The device according to claim 4, wherein the handle defines a pathway that fluidly connects the antiseptic composition and the applicator.

6. The device according to claim 4, wherein the antiseptic composition is stored in a frangible or pierceable container.

7. The device according to claim 6, wherein the handle further comprises one or more actuable elements configured to break or pierce the container.

8. The device according to claim 1, wherein the first material is configured such that the antiseptic composition is wicked along most of the length, or the full length, of the first layer about 30 seconds following initial exposure to the antiseptic composition.

9. The device according to claim 1, wherein the indicia of the second layer is provided at the second end of the first layer such that the indicia is only visible to a user when the antiseptic composition has been wicked along substantially the full length of the first layer.

10. The device according to claim 1, wherein the applicator is circular in shape.

11. The device according to claim 1, wherein the applicator is quadrilateral in shape.

12. The device according to claim 1, wherein the indicia comprises one or more of a color and a symbol.

13. A method of disinfecting skin, comprising:
applying the antiseptic composition to the skin of the patient with the device according to claim 1 until the indicia is at least partially visible to the user.

14. The method according to claim 13, wherein the antiseptic composition is applied to the skin of the patient for at least 30 seconds before the indicia is at least partially visible to the user.

15. A method of disinfecting skin, comprising:
providing a device comprising:
a handle comprising a proximal end, a distal end, a sidewall therebetween, and one or more actuable elements arranged along the sidewall, the sidewall defining an at least partially hollow interior;
a frangible or pierceable container holding an antiseptic composition received within the at least partially hollow interior, the container configured to be broken or pierced by the one or more actuable elements;
an applicator arranged at the distal end of the handle and in fluid communication with the at least partially hollow interior, the applicator configured to, following breaking or piercing of the container, absorb the antiseptic composition, the applicator comprising a top surface and a bottom surface, the bottom surface defining the distal most end of the device and configured to apply the antiseptic composition to a skin of a patient; and
an indicator comprising:
a first layer comprising a first material configured to wick the antiseptic composition, wherein the first material is opaque when dry and is transparent or translucent when wet; and
a second layer comprising a non-wettable material, the second layer comprising at least one indicia that is visible to a user when the first layer is wet, wherein the first layer is configured to progressively change from a first state to a second state as the antiseptic composition is wicked from a first end of the first layer to a second end of the first layer, with the first layer becoming more wet as the composition is wicked from the first end to the second end, allowing progressive exposure of the second layer, wherein the first layer is dry in the first state when the antiseptic composition has not been wicked along the first layer, and the first layer is wet in the second state when the antiseptic composition has been wicked along more than about 50% of the first layer, and
wherein the first material is a wettable material having a surface with a water contact angle of 75 degrees or less and the first material is configured such that the antiseptic composition is wicked across more than about 50% of the first layer about 30 seconds following initial exposure of the first material to the antiseptic composition,
wherein the indicator is arranged on the top surface of the applicator and the second layer of the indicator is arranged between the top surface of the applicator and the first layer of the indicator;
actuating the one or more actuable elements to break or pierce the container; and
applying the antiseptic composition to the skin of the patient until the indicia is at least partially visible.

16. A device comprising:
a handle comprising a proximal end, a distal end, a sidewall therebetween, and one or more actuable elements arranged along the sidewall, the sidewall defining an at least partially hollow interior;
a frangible or pierceable container holding an antiseptic composition received within the at least partially hollow interior, the container configured to be broken or pierced by the one or more actuable elements;
a circular applicator arranged at the distal end of the handle and in fluid communication with the at least partially hollow interior, the applicator configured to, following breaking or piercing of the container, absorb the antiseptic composition, the applicator comprising a top surface and a bottom surface, the bottom surface defining the distal most end of the device and configured to apply the antiseptic composition to a skin of a patient; and
an indicator arranged at least partially on the top surface of the applicator and comprising:
a first layer in fluid communication with the applicator and comprising a first material configured to wick the antiseptic composition, wherein the first material is opaque when dry and is transparent or translucent when wet; and
a second layer arranged between the first layer of the indicator and the top surface of the applicator and comprising a non-wettable material, the second layer comprising at least one indicia that is visible to a user when the first layer is wet,
wherein the first layer is configured to progressively change from the first state to the second state as the antiseptic composition is wicked from a first end of the first layer to a second end of the first layer, with the first layer becoming more wet as the composition is wicked from the first end to the second end, allowing progressive exposure of the second layer, wherein the first layer is dry in a first state when the antiseptic composition has not been wicked along the first layer, and the first layer is wet in a second state when the antiseptic composition has been wicked along more than about 50% of the first layer, and wherein the first material is a wettable material having a surface with a water contact angle of 75 degrees or less and the first material is configured such that the antiseptic composition is wicked across more than about 50% of the first layer about 30 seconds following initial exposure of the first material to the antiseptic composition.

17. A device comprising:

a handle comprising a proximal end, a distal end, a sidewall therebetween, and one or more actuable elements arranged along the sidewall, the sidewall defining an at least partially hollow interior;

a frangible or pierceable container holding an antiseptic composition received within the at least partially hollow interior, the container configured to be broken or pierced by the one or more actuable elements;

a quadrilateral applicator arranged at the distal end of the handle and in fluid communication with the at least partially hollow interior, the applicator configured to, following breaking or piercing of the container, absorb the antiseptic composition, the applicator comprising a top surface and a bottom surface, the bottom surface defining the distal most end of the device and configured to apply the antiseptic composition to a skin of a patient; and an indicator arranged at least partially on the top surface of the applicator and comprising:

a first layer in fluid communication with the applicator and comprising a first material configured to wick the antiseptic composition, wherein the first material is opaque when dry and is transparent or translucent when wet; and a second layer arranged between the first layer of the indicator and the top surface of the applicator and comprising a non-wettable material, the second layer comprising at least one indicia that is visible to a user when the first layer is wet, wherein the first layer is configured to progressively change from the first state to the second state as the antiseptic composition is wicked from a first end of the first layer to a second end of the first layer, with the first layer becoming more wet as the composition is wicked from the first end to the second end, allowing progressive exposure of the second layer, wherein the first layer is dry in a first state when the antiseptic composition has not been wicked along the first layer, and the first layer is wet in a second state when the antiseptic composition has been wicked along more than about 50% of the first layer, and wherein the first material is a wettable material having a surface with a water contact angle of 75 degrees or less and the first material is configured such that the antiseptic composition is wicked across more than about 50% of the first layer about 30 seconds following initial exposure of the first material to the antiseptic composition.

18. The device according to claim 1, wherein the indicia of the second layer is provided along substantially the full length of the first layer such that, progressively, a greater portion of the indicia becomes visible to a user as the antiseptic composition is progressively wicked along the length of the first layer.

* * * * *